United States Patent
Sweeney

(10) Patent No.: US 8,055,517 B2
(45) Date of Patent: *Nov. 8, 2011

(54) OPTIMIZATION OF TIMING FOR DATA COLLECTION AND ANALYSIS IN ADVANCED PATIENT MANAGEMENT SYSTEM

(75) Inventor: Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/955,111

(22) Filed: Nov. 29, 2010

(65) Prior Publication Data

US 2011/0071848 A1    Mar. 24, 2011

Related U.S. Application Data

(63) Continuation of application No. 12/796,082, filed on Jun. 8, 2010, now Pat. No. 7,860,733, which is a continuation of application No. 11/174,922, filed on Jul. 5, 2005, now Pat. No. 7,752,059.

(51) Int. Cl.
G06Q 50/00 (2006.01)
A61B 5/02 (2006.01)
(52) U.S. Cl. ............... 705/3; 705/8; 600/483; 600/301
(58) Field of Classification Search ............ 705/2–3, 705/8; 600/301, 483
See application file for complete search history.

(56) References Cited

U.S. PATENT DOCUMENTS

| 4,561,443 A | 12/1985 | Hogrefe et al. |
| 4,658,831 A | 4/1987 | Reinhard et al. |
| 4,681,111 A | 7/1987 | Silvian |
| 4,705,043 A | 11/1987 | Imran |
| 4,757,816 A | 7/1988 | Ryan et al. |
| 4,793,353 A | 12/1988 | Borkan |
| 4,809,697 A | 3/1989 | Causey, III et al. |
| 4,932,408 A | 6/1990 | Schaldach |
| 4,947,407 A | 8/1990 | Silvian |
| 4,969,464 A | 11/1990 | Callaghan et al. |

(Continued)

FOREIGN PATENT DOCUMENTS

EP    0554955 A1    8/1993

(Continued)

OTHER PUBLICATIONS

"U.S. Appl. No. 11/174,922, Amendment Under 1.312 filed May 20, 2010", 7 pgs.

(Continued)

*Primary Examiner* — Robert Morgan
*Assistant Examiner* — Anita Molina
(74) *Attorney, Agent, or Firm* — Schwegman, Lundberg & Woessner, P.A.

(57) ABSTRACT

Advanced patient management systems include a unit for collecting data from a device associated with a patient, and a host in communication with the unit, the host identifying a time for the device to update data on the device. The system can identify a time for the device to update data associated with the device by developing a histogram of the availability of the device for interrogation. The system can also optimize processing loads for the system by developing a histogram of the time at which the caregiver is most likely to access the system to review the collected and processed data. Methods for optimizing device data update and processing times are also included.

20 Claims, 5 Drawing Sheets

U.S. PATENT DOCUMENTS

| | | |
|---|---|---|
| 5,058,581 A | 10/1991 | Silvian |
| 5,081,987 A | 1/1992 | Nigam |
| 5,113,869 A | 5/1992 | Nappholz et al. |
| 5,117,825 A | 6/1992 | Grevious |
| 5,137,022 A | 8/1992 | Henry |
| 5,241,961 A | 9/1993 | Henry |
| 5,292,343 A | 3/1994 | Blanchette et al. |
| 5,331,966 A | 7/1994 | Bennett et al. |
| 5,336,245 A | 8/1994 | Adams et al. |
| 5,350,411 A | 9/1994 | Ryan et al. |
| 5,379,340 A | 1/1995 | Overend et al. |
| 5,381,798 A | 1/1995 | Burrows |
| 5,383,915 A | 1/1995 | Adams |
| 5,413,594 A | 5/1995 | Williams |
| 5,415,181 A | 5/1995 | Hogrefe et al. |
| 5,458,122 A | 10/1995 | Hethuin |
| 5,476,485 A | 12/1995 | Weinberg et al. |
| 5,481,262 A | 1/1996 | Urbas et al. |
| 5,502,543 A | 3/1996 | Aboujaoude |
| 5,509,927 A | 4/1996 | Epstein et al. |
| 5,522,865 A | 6/1996 | Schulman et al. |
| 5,549,654 A | 8/1996 | Powell |
| 5,586,264 A | 12/1996 | Belknap et al. |
| 5,626,630 A | 5/1997 | Markowitz et al. |
| 5,629,678 A | 5/1997 | Gargano et al. |
| 5,630,836 A | 5/1997 | Prem et al. |
| 5,674,249 A | 10/1997 | De Coriolis et al. |
| 5,683,432 A | 11/1997 | Goedeke et al. |
| 5,713,937 A | 2/1998 | Nappholz et al. |
| 5,720,770 A | 2/1998 | Nappholz et al. |
| 5,741,315 A | 4/1998 | Lee et al. |
| 5,743,267 A | 4/1998 | Nikolic et al. |
| 5,752,976 A | 5/1998 | Duffin et al. |
| 5,752,977 A | 5/1998 | Grevious et al. |
| 5,759,199 A | 6/1998 | Snell et al. |
| 5,766,232 A | 6/1998 | Grevious et al. |
| 5,769,876 A | 6/1998 | Silvian |
| 5,772,586 A | 6/1998 | Heinonen et al. |
| 5,774,501 A | 6/1998 | Halpern et al. |
| 5,791,342 A | 8/1998 | Woodard |
| 5,792,207 A | 8/1998 | Dietrich |
| 5,814,089 A | 9/1998 | Stokes et al. |
| 5,836,983 A | 11/1998 | Weijand et al. |
| 5,843,133 A | 12/1998 | Routh et al. |
| 5,843,139 A | 12/1998 | Goedeke et al. |
| 5,861,014 A | 1/1999 | Familoni |
| 5,861,018 A | 1/1999 | Feierbach |
| 5,862,803 A | 1/1999 | Besson et al. |
| 5,889,474 A | 3/1999 | LaDue |
| 5,899,928 A | 5/1999 | Sholder et al. |
| 5,899,931 A | 5/1999 | Deschamp et al. |
| 5,907,491 A | 5/1999 | Canada et al. |
| 5,917,414 A | 6/1999 | Opplet et al. |
| 5,919,214 A | 7/1999 | Ciciarelli et al. |
| 5,935,078 A | 8/1999 | Feierbach |
| 5,944,659 A | 8/1999 | Flach et al. |
| 5,957,861 A | 9/1999 | Combs et al. |
| 5,999,857 A | 12/1999 | Weijand et al. |
| 6,083,248 A | 7/2000 | Thompson |
| 6,093,146 A | 7/2000 | Filangeri |
| 6,115,636 A | 9/2000 | Ryan |
| 6,141,584 A | 10/2000 | Rockwell et al. |
| 6,169,988 B1 | 1/2001 | Asakura |
| 6,170,488 B1 | 1/2001 | Spillman, Jr. et al. |
| 6,185,452 B1 | 2/2001 | Schulman et al. |
| 6,200,264 B1 | 3/2001 | Satherley et al. |
| 6,203,495 B1 | 3/2001 | Bardy |
| 6,206,835 B1 | 3/2001 | Spillman, Jr. et al. |
| 6,208,894 B1 | 3/2001 | Schulman et al. |
| 6,213,942 B1 | 4/2001 | Flach et al. |
| 6,216,038 B1 | 4/2001 | Hartlaub et al. |
| 6,221,011 B1 | 4/2001 | Bardy |
| 6,223,083 B1 | 4/2001 | Rosar |
| 6,236,889 B1 | 5/2001 | Soykan et al. |
| 6,240,317 B1 | 5/2001 | Villaseca et al. |
| 6,250,309 B1 | 6/2001 | Krichen et al. |
| 6,261,230 B1 | 7/2001 | Bardy |
| 6,263,245 B1 | 7/2001 | Snell et al. |
| 6,263,246 B1 | 7/2001 | Goedeke et al. |
| 6,263,247 B1 | 7/2001 | Mueller et al. |
| 6,270,457 B1 | 8/2001 | Bardy |
| 6,289,238 B1 | 9/2001 | Besson et al. |
| 6,292,698 B1 | 9/2001 | Duffin et al. |
| 6,295,466 B1 | 9/2001 | Ishikawa et al. |
| 6,298,271 B1 | 10/2001 | Weijand |
| 6,300,903 B1 | 10/2001 | Richards et al. |
| 6,304,788 B1 | 10/2001 | Eady et al. |
| 6,312,378 B1 | 11/2001 | Bardy |
| 6,319,200 B1 | 11/2001 | Lai et al. |
| 6,329,929 B1 | 12/2001 | Weijand et al. |
| 6,330,640 B1 | 12/2001 | Williams et al. |
| 6,345,203 B1 | 2/2002 | Mueller et al. |
| 6,349,234 B2 | 2/2002 | Pauly et al. |
| 6,363,130 B1 | 3/2002 | Bontu et al. |
| 6,363,282 B1 | 3/2002 | Nichols et al. |
| 6,418,346 B1 | 7/2002 | Nelson et al. |
| 6,427,088 B1 | 7/2002 | Bowman, IV et al. |
| 6,442,432 B2 | 8/2002 | Lee |
| 6,442,433 B1 | 8/2002 | Linberg |
| 6,477,424 B1 | 11/2002 | Thompson et al. |
| 6,480,745 B2 | 11/2002 | Nelson et al. |
| 6,635,014 B2 | 10/2003 | Starkweather et al. |
| 6,735,630 B1 | 5/2004 | Gelvin et al. |
| 6,922,388 B1 | 7/2005 | Laroia |
| 7,016,944 B1 | 3/2006 | Meyer et al. |
| 7,117,017 B2 | 10/2006 | Chen et al. |
| 7,187,979 B2 | 3/2007 | Haubrich et al. |
| 7,266,379 B2 | 9/2007 | Blight et al. |
| 7,490,122 B2 | 2/2009 | Horvitz et al. |
| 7,752,059 B2 | 7/2010 | Sweeney |
| 7,860,733 B2 | 12/2010 | Sweeney |
| 2001/0012955 A1 | 8/2001 | Goedeke et al. |
| 2001/0023360 A1 | 9/2001 | Nelson et al. |
| 2001/0025137 A1 | 9/2001 | Webb et al. |
| 2001/0025189 A1 | 9/2001 | Haueter et al. |
| 2001/0027331 A1 | 10/2001 | Thompson |
| 2001/0027349 A1 | 10/2001 | Eady et al. |
| 2001/0029321 A1 | 10/2001 | Beetz et al. |
| 2001/0031998 A1 | 10/2001 | Nelson et al. |
| 2001/0037056 A1 | 11/2001 | Nunome |
| 2001/0039372 A1 | 11/2001 | Yasushi et al. |
| 2001/0044588 A1 | 11/2001 | Mault |
| 2001/0047125 A1 | 11/2001 | Quy |
| 2001/0049275 A1 | 12/2001 | Pierry et al. |
| 2001/0049554 A1 | 12/2001 | Ruiz et al. |
| 2001/0051764 A1 | 12/2001 | Bardy |
| 2001/0051787 A1 | 12/2001 | Haller et al. |
| 2002/0013517 A1 | 1/2002 | West et al. |
| 2002/0013518 A1 | 1/2002 | West et al. |
| 2002/0013538 A1 | 1/2002 | Teller |
| 2002/0013613 A1 | 1/2002 | Haller et al. |
| 2002/0013614 A1 | 1/2002 | Thompson |
| 2002/0019584 A1 | 2/2002 | Schulze et al. |
| 2002/0019586 A1 | 2/2002 | Teller et al. |
| 2002/0028988 A1 | 3/2002 | Suzuki et al. |
| 2002/0032470 A1 | 3/2002 | Linberg |
| 2002/0040234 A1 | 4/2002 | Linberg |
| 2002/0052539 A1 | 5/2002 | Haller et al. |
| 2002/0072785 A1 | 6/2002 | Nelson et al. |
| 2002/0082665 A1 | 6/2002 | Haller et al. |
| 2002/0083025 A1 | 6/2002 | Robarts et al. |
| 2004/0064293 A1 | 4/2004 | Hamilton et al. |
| 2004/0127958 A1 | 7/2004 | Mazar et al. |
| 2005/0186980 A1 | 8/2005 | Richharia et al. |
| 2006/0120339 A1 | 6/2006 | Akiyama et al. |
| 2007/0011028 A1 | 1/2007 | Sweeney |
| 2008/0306678 A1 | 12/2008 | Miyawaki |
| 2009/0312029 A1* | 12/2009 | Ananthanarayanan et al. ............... 455/450 |
| 2010/0011251 A1* | 1/2010 | Mannar et al. ............ 714/32 |
| 2010/0250287 A1 | 9/2010 | Sweeney |
| 2011/0093294 A1* | 4/2011 | Elahi et al. ............... 705/3 |

FOREIGN PATENT DOCUMENTS

| | | |
|---|---|---|
| JP | 11015715 | 1/1999 |

OTHER PUBLICATIONS

"U.S. Appl. No. 11/174,922, Examiner Interview Summary mailed Jan. 20, 2010", 3 pgs.
"U.S. Appl. No. 11/174,922, Non Final Office Action mailed Apr. 29, 2009", 14 pgs.
" U.S. Appl. No. 11/174,922, Notice of Allowance mailed Feb. 23, 2010", 12 pgs.
"U.S. Appl. No. 11/174,922, Response filed Aug. 11, 2009 to Non Final Office Action mailed Apr. 29, 2009", 13 pgs.
"U.S. Appl. No. 11/174,922, Supplemental Amendment and Response filed Jan. 22, 2010", 8 pgs.
"U.S. Appl. No. 11/174,922, Supplemental Amendment and Response filed Feb. 4, 2010", 8 pgs.
"U.S. Appl. No. 11/174,922, Supplemental Amendment and Response filed Nov. 25, 2009", 7 pgs.
"U.S. Appl. No. 12/796,082, Notice of Allowance mailed Aug. 17, 2010", 14 pgs.
Clancy, Sharon, "Keeping It Chilled", Commercial Motor. Sutton: Mar. 25, 2004, vol. 199, Iss. 5072; p. 58, 4 pgs.

* cited by examiner

OPTIMIZATION OF TIMING FOR DATA COLLECTION AND ANALYSIS IN ADVANCED PATIENT MANAGEMENT SYSTEM

CROSS REFERENCE TO RELATED APPLICATION

This application is a continuation of U.S. application Ser. No. 12/796,082, filed Jun. 8, 2010, now issued as U.S. Pat. No. 7,860,733, which is a continuation of U.S. application Ser. No. 11/174,922, filed Jul. 5, 2005, now issued as U.S. Pat. No. 7,752,059, the contents of which are incorporated herein by reference, and the priority of each of which is claimed herein.

TECHNICAL FIELD

The present disclosure relates generally to advanced patient management systems. More particularly, the present disclosure relates to the optimization of the timing for data collection and analysis in advanced patient management systems.

BACKGROUND

Management of patients with chronic disease consumes a significant proportion of the total health care expenditure in the United States. Many of these diseases, such as heart disease, are widely prevalent and have significant annual incidences as well. Patients with chronic heart disease can receive implanted cardiac rhythm management (CRM) devices such as pacemakers, implantable cardioverter defibrillators (ICDs), and heart failure cardiac resynchronization therapy (CRT) devices to provide treatment for the disease.

Advanced patient management (APM) systems allow caregivers to remotely gather and analyze data associated with a patient and the patient's CRM device. APM systems provide a vast amount of information to the caregiver in an automated manner. This information can provide insights into a patient's well being and help the caregiver predict significant changes in a patient's health, such as a decompensation event associated with a heart attack. However, the time lag between when data is updated on a CRM device and when it is collected, analyzed, and presented for review by the APM system can reduce the timeliness of the information provided to the caregiver.

For example, CRM devices can update device data stored in the CRM device memory at periodic intervals, such as once per day. One example of device data that can be updated periodically by a CRM device is heart rate variability. For example, the CRM device can be programmed to update an average heart rate variability for a patient once per day. The timing for these device updates is usually arbitrarily set at the time at which the CRM device is originally initiated prior to or at the time of implantation. There can be a significant time lag due to a lack of coordination between the device data update time by a CRM device and the time at which an APM system collects data from (e.g., interrogates) the device.

For example, a CRM device can be arbitrarily set to update device data at time-of-day A in day 1, as shown in FIG. 1. Assume that the APM system interrogates the CRM device at time-of-day B in day 2, and that the caregiver accesses the APM system to review the information that the APM system has collected from the device and analyzed at time-of-day C. Although the entire interval or lag D between device data (time-of-day A) and caregiver review (time-of-day C) spans two days, it is a relatively short period, so that the caregiver is reviewing recently acquired and analyzed information.

However, in another example shown in FIG. 2, assume again that the CRM device is arbitrarily set to update device data at time-of-day A earlier in day 1, and that the APM system interrogates the CRM device at time-of-day B in day 2. Also assume that the caregiver does not review the information on the APM system until later at time-of-day C. In this scenario, lag D is more significant, resulting in less-timely information being provided to the caregiver. In a worst-case scenario based on daily device updates and interrogations, the caregiver could be presented with information that is forty-eight (48) hours old. It is desirable to minimize lag D so that the caregiver is given data that is as current as possible so that the caregiver can make timely decisions regarding a patient's health.

In addition to the potential time lag problems associated with the collection of data, an APM system can potentially be used to analyze data associated with thousands or millions of patients at any given time. It is therefore desirable to optimize analysis of data on the APM system such that the APM system can efficiently analyze each patient's data while presenting current data to each caregiver as the caregiver accesses the APM system.

SUMMARY

The present disclosure relates generally to advanced patient management systems. More particularly, the present disclosure relates to the optimization of the timing for data collection and analysis in advanced patient management systems.

According to one aspect, an advanced patient management system includes a unit for collecting data from a device associated with a patient, and a host in communication with the unit, the host identifying a time for the unit to collect data from the device.

According to another aspect, a method for collecting and analyzing data associated with a device of a patient by an advanced patient management system includes: identifying a time period during which the device is most likely to be available for data collection, setting a device update time based on the time period during which the device is most likely to be available for data collection, and setting a data collection time based on the time period during which the device is most likely to be available for data collection.

According to yet another aspect, a method for gathering and processing data associated with a device of a patient by an advanced patient management system includes: identifying a time period during which data associated with the patient is most likely to be accessed by a caregiver, setting an analysis time for the data based on the time period during which the data associated with the patient is most likely to be accessed, and analyzing the data at the analysis time.

The above summary is not intended to describe each disclosed embodiment or every implementation of the present invention. The figures and the detailed description that follow further describe these embodiments.

DESCRIPTION OF THE DRAWINGS

Aspects of the invention may be more completely understood in consideration of the following detailed description of various embodiments of the invention in connection with the accompanying drawings, in which.

Figure 1:
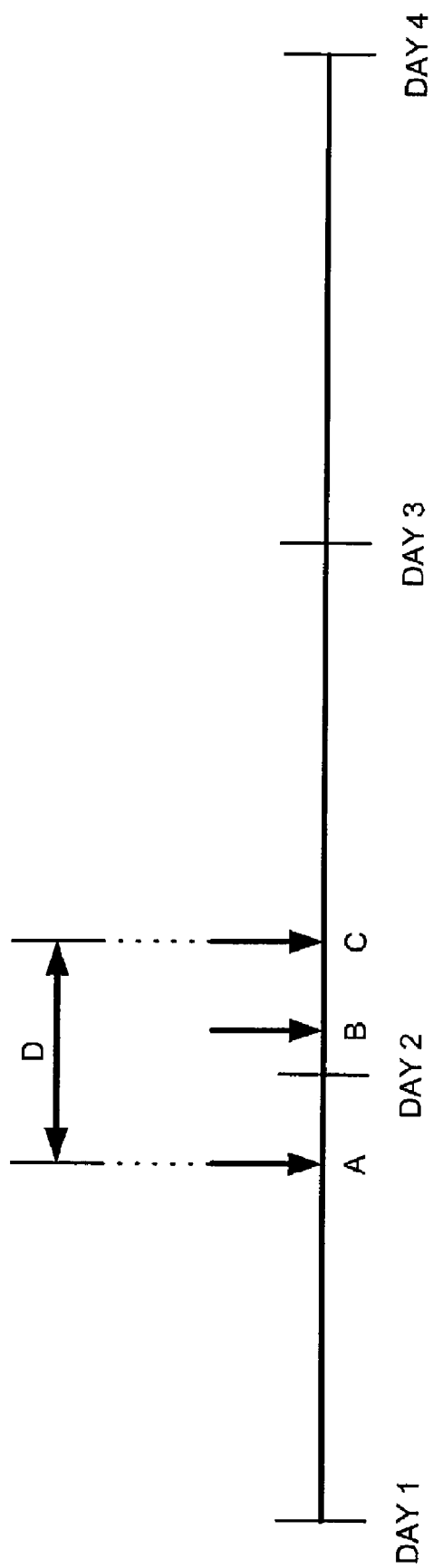
FIG. 1 illustrates an example timeline for device data update, interrogation, and review of data associated with a patient's device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present disclosure relates generally to advanced patient management systems. More particularly, the present disclosure relates to the optimization of the timing for data collection and analysis in advanced patient management systems.

The term "patient" is used herein to mean any individual from whom information is collected. The term "caregiver" is used herein to mean any provider of services, such as health care providers including, but not limited to, nurses, doctors, and other health care provider staff.

Figure 3:
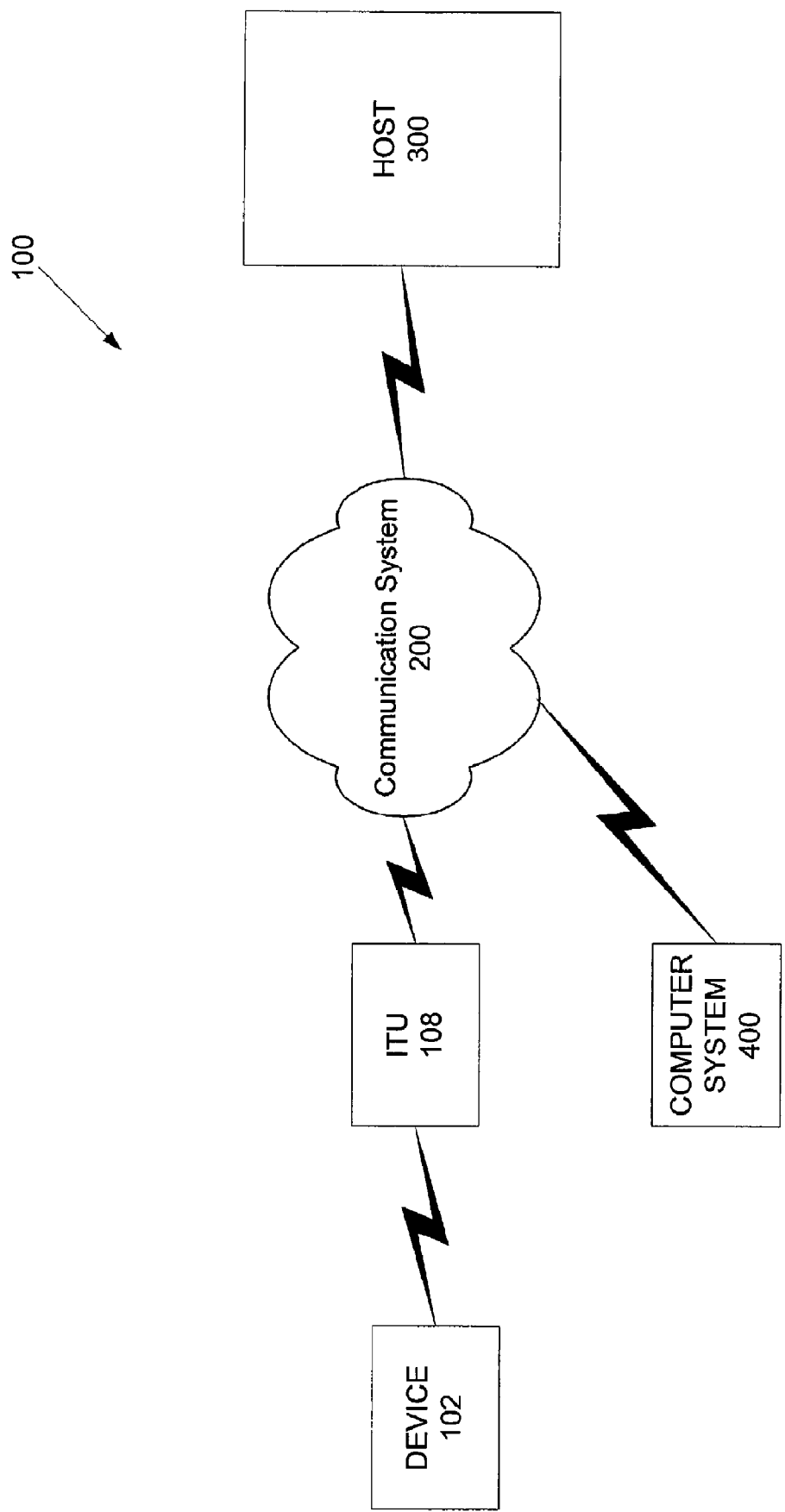
FIG. 3 illustrates an example advanced patient management system.

FIG. 3 illustrates an example advanced patient management system 100 made in accordance with the present invention. Advanced patient management (APM) system 100 generally includes the following components: a device 102, an interrogator/transceiver unit 108, a communication system 200, a host 300, and a computer system 400. Each component of the APM system 100 can communicate using the communication system 200. Some components may also communicate directly with one another.

Device 102 can be an implantable device or an external device that provides one or more of the following functions with respect to a patient: (1) sensing, (2) data analysis, and (3) therapy. For example, in one embodiment, device 102 is either an implanted or external device used to measure a variety of physiological, subjective, and environmental conditions of a patient using electrical, mechanical, and/or chemical means. Device 102 can be configured to automatically gather data or can require manual intervention by the patient. Device 102 can be configured to store data related to the physiological and/or subjective measurements and/or transmit the data to the communication network 200 using a variety of methods, described in detail below. Although a single device 102 is illustrated in the example embodiment shown, more devices can be used for a given patient.

In the example shown, device 102 is a cardiac rhythm management (CRM) device that is implanted within a patient. Examples of CRM devices include pacemakers, cardiac resynchronization management devices, defibrillators, etc. CRM devices can have the ability to sense and communicate, and may also provide therapy.

Figure 2:
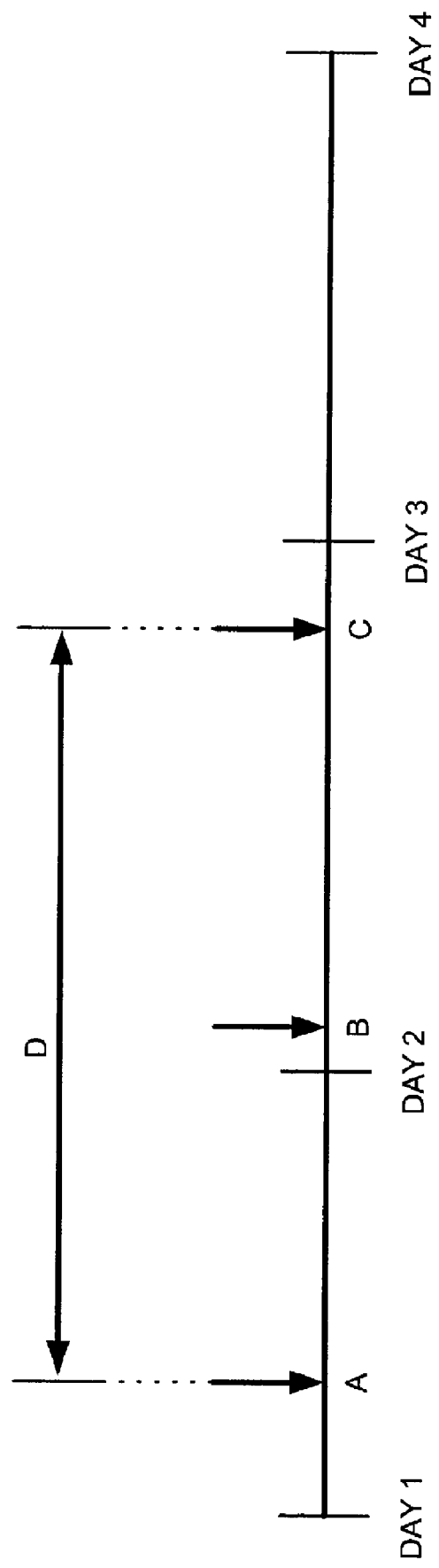
FIG. 2 illustrates another example timeline for device data update, interrogation, and review of data associated with a patient's device.

In the example shown, device 102 is configured to periodically update data associated with the patient and/or device (collectively referred to as "device data") and store this data in memory. These device data updates can, for example, be configured to occur hourly, daily, weekly, or monthly. In the examples shown, device 102 is configured to update device data daily. For example, device 102 can be configured to update physiological measurements associated with a patient at a given time each day. Examples of such physiological measurements include, without limitation, electrical cardiac activity (e.g., heart rate, heart rate variability, etc.), transpulmonary impedance, physical motion, temperature, activity, blood pressure, breathing patterns, ejection fractions, blood viscosity, blood chemistry, and blood glucose levels. The time-of-day at which these device data updates occur is typically initially set prior to or at implantation of device 102. See, e.g., time-of-day A shown in FIGS. 1 and 2 described above. The time-of-day can be reset after implantation by, for example, APM system 100, as described further below.

The example advanced patient management system 100 also includes one or more interrogator/transceiver units ("ITUs"), such as example ITU 108. The ITU 108 can perform one or more of the following functions: (1) data retrieval; (2) data storage; (3) data analysis; and (4) data communication. For example, the ITU 108 facilitates communications between the device 102 and the host 300 using the communication system 200. The ITU 108 can, periodically or in real-time, collect and download into memory (e.g., interrogate) clinically relevant patient data from device 102. This data can include, in the CRM device context, for example, P and R-wave measurements, other physiological data (e.g., HRV, activity, heart rates, etc.), pacing, shocking events, lead impedances, pacing thresholds, battery voltage, capacitor charge times, ATR episodes with electrograms, tachycardia episodes with electrograms, histogram information, and any other clinical information necessary to ensure patient health and proper device function. The ITU 108 can also be configured to ask the patient to report symptoms or current quality of life indications. The data is sent to the ITU 108 by the device 102 in real-time or is periodically uploaded from buffers in the CRM device.

In the examples described herein, a single ITU 108 is described that is located in the home of a patient. The device 102 is therefore generally available for interrogation by the ITU 108 when the patient is at home. In other embodiments, multiple ITUs 108 can be placed, for example, at home and at work so that the availability for interrogation of device 102 is increased.

Additional details regarding an ITU, such as ITU 108, and how an ITU can function as part of an APM system, such as APM system 100, can be found in U.S. patent application Ser. No. 10/330,677, filed on Dec. 27, 2002 and entitled "Advanced Patient Management System Including Interrogator/Transceiver Unit," the entirety of which is hereby incorporated by reference.

Communication system 200 provides for communications between and among the various components of the APM system 100, such as the device 102, ITU 108, host 300, and computer system 400. Communications system 200 can be, for example, a local area network (LAN), wide area network (WAN), or the Internet. A variety of communication methods and protocols can be used to facilitate communication between device 102, ITU 108, communication system 200, host 300, and computer system 400. For example, wired and wireless communications methods can be used. Wired communication methods include, for example and without limitation, traditional copper-line communications such as DSL, broadband technologies such as ISDN and cable modems, and fiber optics. Wireless communication methods include cellular, satellite, radio frequency (RF), Infrared, etc.

In the example embodiment illustrated, host 300 includes one or more computers that store patient information in one or more databases. Host 300 also analyzes the data related to a patient and provides timely and predictive assessments of the patient's well-being. For example, host 300 can store historical data associated with a patient, as well as new data that is transmitted by ITU 108 to host 300. Host 300 can analyze this data and present the analyzed data to the caregiver in one or more formats, as described below. For example, host 300 can compare new heart rate variability data from the CRM device 102 to historical variability levels and provide the caregiver with statistical information related to any changes in heart rate variability over time.

A caregiver can access host 300 using, for example, computer system 400 to review patient data that has been collected and analyzed by APM system 100. For example, in one embodiment, the caregiver can access information on host 300 via a secure web interface over the Internet. In another embodiment, the data collected and analyzed by APM system 100 is delivered to the caregiver's hospital computer system for access by the caregiver. Other electronic delivery methods, such as email, facsimile, etc., can also be used for distribution to the caregiver.

Figure 4:
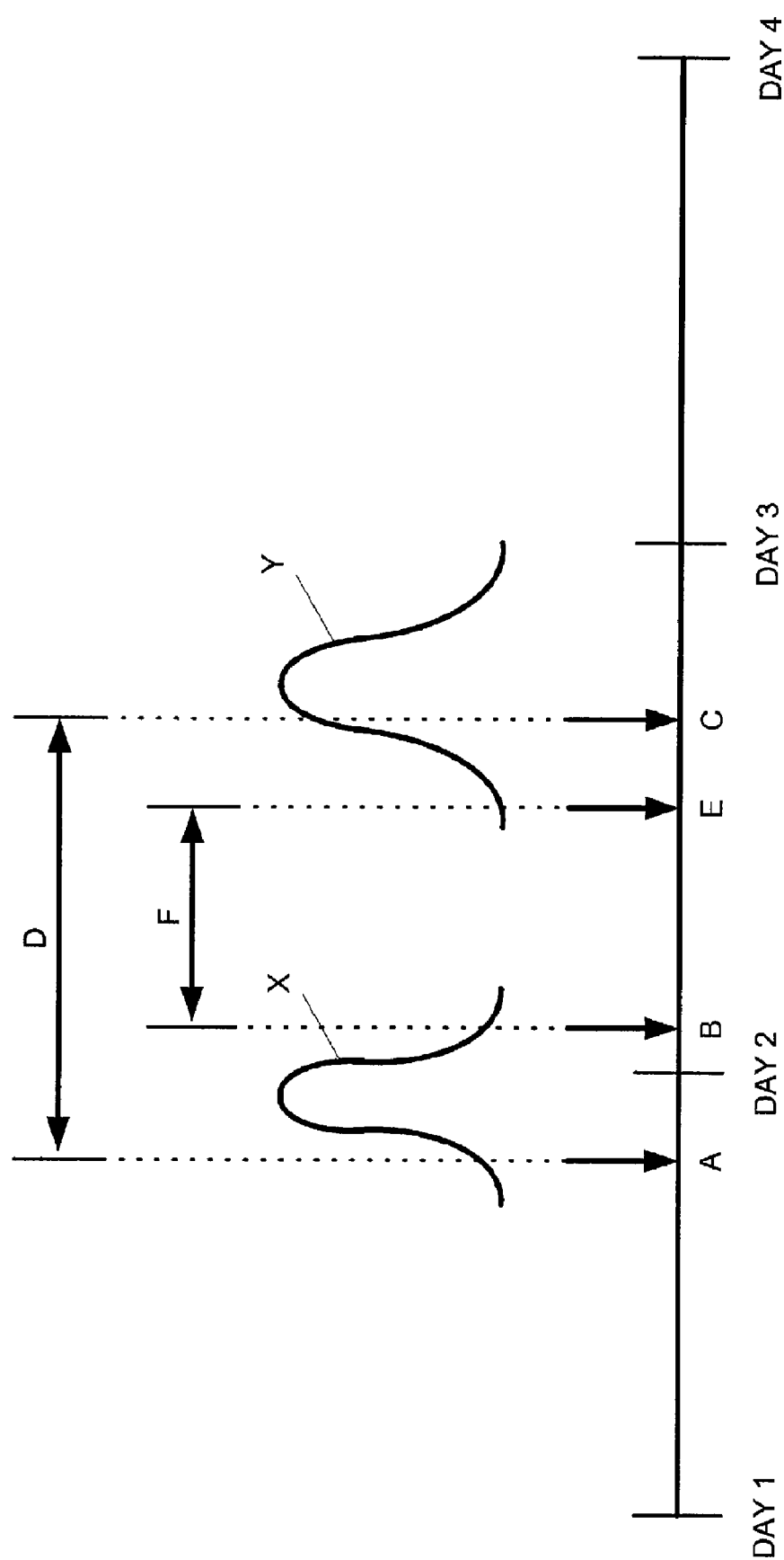
FIG. 4 illustrates another example timeline for device data update, interrogation, and review of data associated with a patient's device.

Referring now to FIG. 4, it is desirable to minimize the interval or lag D between the time-of-day at which device data is updated by device 102 (time-of-day A) and the time-of-day at which the caregiver accesses the APM system 100 to review information associated with the patient (time-of-day C). In general, it is desirable to minimize the lag D so that the caregiver is presented with timely information based on data that has been recently updated, collected, and analyzed.

As noted above, the time-of-day A at which device 102 is set to update device data is typically initially set prior to or during implantation of device 102 in the patient. It is desirable to set the time-of-day A (at which device data update occurs) in view of time-of-day B (at which device 102 is interrogated by ITU 108 to retrieve the updated device data) to minimize lag D so that collected data is as timely as possible.

In the example shown in FIG. 4, APM system 100 is configured to develop a time-of-day histogram X for a patient to determine when a patient's CRM device 102 is most likely to be available for interrogation by ITU 108. This histogram X can be developed over a period of time such as a week or month. For example, during an initialization period, ITU 108 can be configured to periodically search for device 102 at different times of the day and record the time periods during which device 102 is available to ITU 108. ITU 108 and/or host 300 can then develop histogram X that represents the probability versus time-of-day that device 102 is typically available for interrogation by ITU 108.

Time-of-day A for data update on device 102 and time-of-day B for interrogation can be set using histogram X. For example, time-of-day B can be set to occur when there is high or maximum probability that device 120 will be available for interrogation by ITU 108. Time-of-day A for data update on device 102 can be set just prior to the time-of-day B. In one embodiment, time-of-day A is set to a time prior to time-of-day B at which there is a low probability (e.g., 2%) that the patient will be available for interrogation. In another embodiment, time-of-day A is set to a pre-selected interval before time-of-day B for interrogation.

In the examples described herein, APM system 100 can communicate with device 102 through ITU 108 to set time-of-day A for data update on device 102. In this manner, the timing for device data update can be optimized based on the timing for interrogation.

In addition to optimizing the time-of-day A for device data update and time-of-day B for interrogation, APM system 100 can also optimize time-of-day C at which information related to the data collected by APM system 100 is available to the caregiver. For example, as shown in FIG. 4, APM system 100 can develop a time-of-day histogram Y to represent the probability versus time-of-day at which the caregiver will check the patient's information on APM system 100. For example, during an initialization period, APM system 100 can be configured to log times at which the caregiver accesses the APM system to review patient information.

After an initialization period, histogram Y can be created to represent the most likely times at which the caregiver will access the APM system to review the patient's information. Histogram Y can be used to optimize when data collected by APM system 100 is analyzed and presented for review by the caregiver. For example, a time-of-day E at which APM system 100 should complete analysis of patient data can be set just prior to the most likely time that the caregiver will access the APM system based on histogram Y. In one embodiment, time-of-day E is set to a time when there is a low-probability (e.g., 2%) that the caregiver has already accessed the APM system based on histogram Y. In an alternative embodiment, the caregiver can manually set the time-of-day at which the caregiver wants analyzed information to be available.

The APM system 100 can be programmed to process the device data collected from device 102 (at time-of-day B) at any time during interval F between time-of-days B and E to assure that the information is available for the caregiver at the most likely time-of-day for the caregiver to access the APM system 100. In the examples shown, interval F is utilized by APM system 100 to shift analysis of device data to an optimal time during interval F so that the computational load for APM system 100 is balanced. In this manner, host 300 can efficiently process data for thousands or millions of patients by distributing load over the interval F for each patient.

In the examples shown, histograms X and Y and time-of-days B and E are calculated using known statistical methods. For example, the times-of-day when the device is found to be available for interrogation can be grouped into 15 minute bins to form the histogram X and the times-of-day when the caregiver accesses the APM system 100 can be grouped into 15 minute bins to form the histogram Y. Dividing each bin in X or Y by the total number of entries contained in X or Y, respectively, converts X or Y into probability functions versus time-of-day. Time B can be selected to be a time when there is a high (e.g., 98%) cumulative probability that the device is available for interrogation while time E can be selected to be a time when there is a low (e.g., 2%) cumulative probability that the caregiver have already accessed the APM system 100.

In some embodiments, time-of-day histograms are calculated for each day, week, or weekday/weekend. For example, a caregiver may have a schedule that allows the caregiver to check patient data early in the morning on weekdays and later in the afternoon on weekends. Different time-of-day histograms Y can therefore be created for the given caregiver to assure optimal data is presented to the caregiver based on the differing schedules. In addition, different delivery methods can also be used so that, for example, the data can be available on the APM system at a given time during the week and can be delivered wirelessly to the caregiver's handheld device on weekends.

In yet other embodiments, the time-of-day histograms X and Y can be recalculated on a periodic basis to account for changes in a patient or caregiver schedule. For example, if a patient switches from working a day shift to working a night shift during the week, the most likely time that the patient's device will be available for interrogation by the ITU located in the patient's home is during the daytime. By developing a new time-of-day histogram X at periodic intervals, these types of schedule changes can be accommodated.

Figure 5:
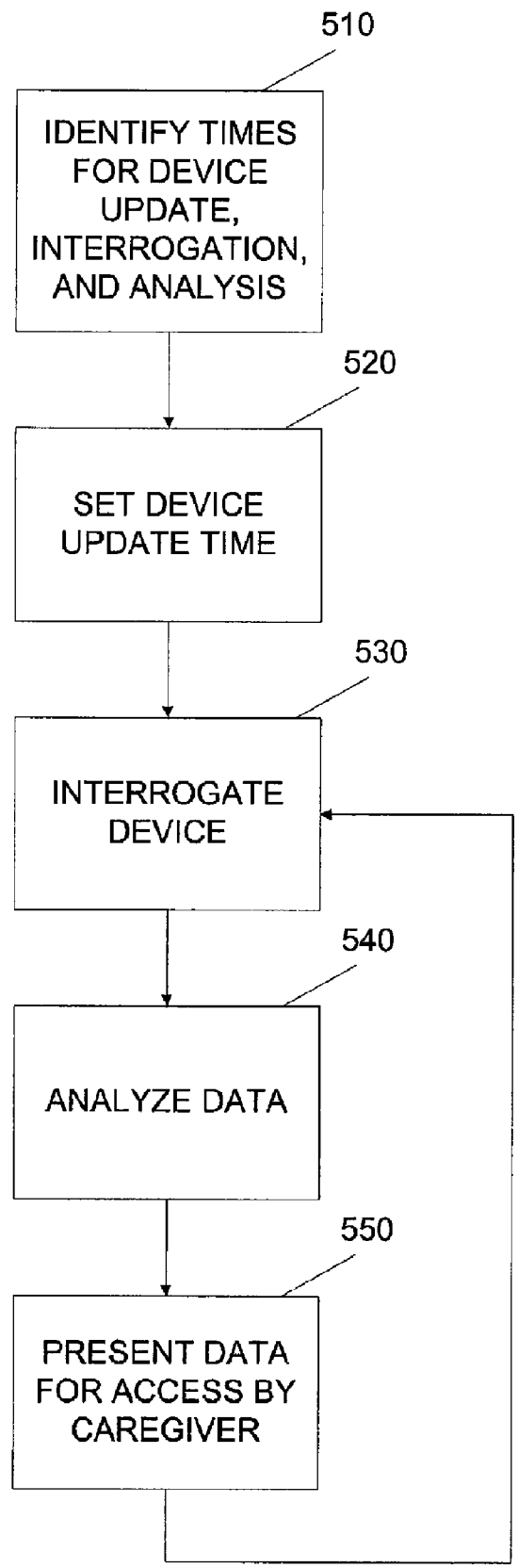
FIG. 5 illustrates an example method for an advanced patient management system.

Referring now to FIG. 5, an example method for an APM system such as system 100 described above is illustrated. In operation 510, the optimal times-of-day for device data update, interrogation, and analysis are set. As described above, for the examples herein these times are set by developing one or more time-of-day histograms. For example, the time-of-day for device data update can be set after the ITU periodically searches for the device to develop a time-of-day histogram to identify at which times the device is most likely to be available for interrogation. The optimal analysis timing can similarly be created using a time-of-day histogram developed by monitoring access of the APM system by the caregiver.

Next, in operation 520, the APM system resets the timing for device data update for the device based on the time-of-day histogram. In the example illustrated herein, the APM system can reset the timing for device data update by sending a wireless instruction through the ITU to the device. Control is then passed to operation 530, and the ITU attempts to interrogate the device at the scheduled interrogation time-of-day.

Next, at operation 540, the data gathered by the ITU from the device is analyzed by the host at an optimal time-of-day prior to the most likely time at which the caregiver will access the data. Next, in operation 550, the host presents the analyzed data for access by the caregiver. Control is then passed back to operation 530, and the ITU interrogates the device at the next time period (e.g., daily, weekly, etc.).

The systems and methods of the present disclosure can be implemented using a system as shown in the various figures disclosed herein including various devices and/or programmers, including implantable or external devices. Accordingly, the methods of the present disclosure can be implemented: (1) as a sequence of computer implemented steps running on the system; and (2) as interconnected modules within the system. The implementation is a matter of choice dependent on the performance requirements of the system implementing the method of the present disclosure and the components selected by or utilized by the users of the method. Accordingly, the logical operations making up the embodiments of the method of the present disclosure described herein can be referred to variously as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

What is claimed is:

1. A patient management system, comprising:
    an ambulatory patient device configured to be associated with a patient; and
    a unit capable of being wirelessly communicatively coupled to the ambulatory patient device, wherein the ambulatory patient device is configured to:
        identify a time period during which the ambulatory patient device is forecasted to be able to communicate with the unit based on a history of availability;
        determine a data update time when the ambulatory patient device updates patient data by updating stored physiological measurements of the patient data in a memory of the ambulatory patient device, the data update time being before the time period during which the ambulatory patient device is forecasted to be able to communicate with the unit; and
        schedule an update of the patient data at the data update time.

2. The system of claim 1, wherein to identify the time period during which the ambulatory patient device is forecasted to be able to communicate with the unit, the ambulatory patient device is further configured to:
    calculate and maintain a histogram of when the ambulatory patient device is able to communicate with the unit; and
    reference the histogram to identify the time period during which the ambulatory patient device is forecasted to be able to communicate with the unit.

3. The system of claim 2, wherein to calculate and maintain the histogram, the ambulatory patient device is further configured to:
    develop a new histogram at a periodic interval.

4. The system of claim 2, wherein to calculate and maintain the histogram, the ambulatory patient device is further configured to:
    calculate and maintain a histogram for a first day of a week; and
    calculate and maintain a histogram for a second day of the week, and wherein to reference the histogram to identify the time period during which the ambulatory patient device is forecasted to be able to communicate with the unit, the ambulatory patient device is further configured to:
    reference the histogram for the first day or the histogram for the second day based on which day the ambulatory patient device is forecasted to be able to communicate with the unit.

5. The system of claim 1, wherein to determine the data update time when the ambulatory patient device updates patient data, the ambulatory patient device is further configured to set the data update time at a pre-selected interval before the time period during which the ambulatory patient device is forecasted to be able to communicate with the computer host.

6. The system of claim 1, wherein the ambulatory patient device is an implantable medical device.

7. A method for gathering and processing patient data by a computer host in a patient management system, the patient data received from an ambulatory patient device, the method comprising:
    identifying, at a computer system, a time period during which the ambulatory patient device is forecasted to be able to communicate with the computer host based on a history of availability;
    determining, at the computer system, a data update time when the ambulatory patient device updates patient data by updating stored physiological measurements of the patient data in a memory of the ambulatory patient device, the data update time being before the time period during which the ambulatory patient device is forecasted to be able to communicate with the computer host; and
    scheduling, using the computer system, the ambulatory patient device to update the patient data at the data update time.

8. The method of claim 7, wherein identifying the time period during which the ambulatory patient device is forecasted to be able to communicate with the computer host comprises:
- calculating and maintaining a histogram of when the ambulatory patient device is able to communicate with the computer host; and
- referencing the histogram to identify the time period during which the ambulatory patient device is forecasted to be able to communicate with the computer host.

9. The method of claim 8, wherein calculating and maintaining the histogram comprises:
- developing a new histogram at a periodic interval.

10. The method of claim 8, wherein calculating and maintaining the histogram comprises:
- calculating and maintaining a histogram for a first day of a week; and
- calculating and maintaining a histogram for a second day of the week, and wherein referencing the histogram to identify the time period during which the ambulatory patient device is forecasted to be able to communicate with the computer host comprises:
- referencing the histogram for the first day or the histogram for the second day based on which day the ambulatory patient device is forecasted to be able to communicate with the computer host.

11. The method of claim 7, wherein determining the data update time when the ambulatory patient device updates patient data comprises setting the data update time at a preselected interval before the time period during which the ambulatory patient device is forecasted to be able to communicate with the computer host.

12. The method of claim 7, wherein the ambulatory device comprises the computer system, and wherein the operations of method 7 are performed by the ambulatory device.

13. The method of claim 7, wherein the computer host comprises the computer system, and wherein the operations of claim 7 are performed by the computer host.

14. The method of claim 7, wherein the ambulatory device is an implantable medical device.

15. A non-transitory machine readable medium comprising instructions for gathering and processing patient data received from an ambulatory patient device at a computer host in a patient management system, which when executed by a machine, cause the machine to:
- identify, at a computer system, a time period during which the ambulatory patient device is forecasted to be able to communicate with the computer host based on a history of availability;
- determine, at the computer system, a data update time when the ambulatory patient device updates patient data by updating stored physiological measurements of the patient data in a memory of the ambulatory patient device, the data update time being before the time period during which the ambulatory patient device is forecasted to be able to communicate with the computer host; and
- schedule, using the computer system, the ambulatory patient device to update the patient data at the data update time.

16. The non-transitory machine readable medium of claim 15, wherein the instructions to identify the time period during which the ambulatory patient device is forecasted to be able to communicate with the computer host comprise instructions, which when executed by the machine, cause the machine to:
- calculate and maintain a histogram of when the ambulatory patient device is able to communicate with the computer host; and
- reference the histogram to identify the time period during which the ambulatory patient device is forecasted to be able to communicate with the computer host.

17. The non-transitory machine readable medium of claim 16, wherein the instructions to calculate and maintain the histogram comprise instructions, which when executed by the machine, cause the machine to:
- develop a new histogram at a periodic interval.

18. The non-transitory machine readable medium of claim 16, wherein the instructions to calculate and maintain the histogram comprise instructions, which when executed by the machine, cause the machine to:
- calculate and maintain a histogram for a first day of a week; and
- calculate and maintain a histogram for a second day of the week, and wherein the instructions to reference the histogram to identify the time period during which the ambulatory patient device is forecasted to be able to communicate with the computer host comprise instructions, which when executed by the machine, cause the machine to:
- reference the histogram for the first day or the histogram for the second day based on which day the ambulatory patient device is forecasted to be able to communicate with the computer host.

19. The non-transitory machine readable medium of claim 15, wherein the instructions to determine the data update time when the ambulatory patient device updates patient data comprise instructions, which when executed by the machine, cause the machine to set the data update time at a pre-selected interval before the time period during which the ambulatory patient device is forecasted to be able to communicate with the computer host.

20. The non-transitory machine readable medium of claim 15, wherein the ambulatory device comprises the computer system, and wherein the operations of method 15 are performed by the ambulatory device.

* * * * *

UNITED STATES PATENT AND TRADEMARK OFFICE
CERTIFICATE OF CORRECTION

| | | |
|---|---|---|
| PATENT NO. | : 8,055,517 B2 | Page 1 of 1 |
| APPLICATION NO. | : 12/955111 | |
| DATED | : November 8, 2011 | |
| INVENTOR(S) | : Sweeney | |

It is certified that error appears in the above-identified patent and that said Letters Patent is hereby corrected as shown below:

In column 9, line 35, in Claim 12, delete "method 7" and insert -- claim 7 --, therefor.

In column 10, line 50, in Claim 20, delete "method 15" and insert -- claim 15 --, therefor.

Signed and Sealed this
Seventeenth Day of January, 2012

David J. Kappos
*Director of the United States Patent and Trademark Office*